United States Patent
Abdel-Malek et al.

[19]

[11] Patent Number: 6,137,527
[45] Date of Patent: Oct. 24, 2000

[54] SYSTEM AND METHOD FOR PROMPT-RADIOLOGY IMAGE SCREENING SERVICE VIA SATELLITE

[75] Inventors: Aiman Albert Abdel-Malek, Schenectady; Kathryn Eike Dudding, Clifton Park; Bruce Gordon Barnett, Troy, all of N.Y.; Charles Andrew Tompkins, Monmouth Junction; Mohsen Gharabaghloo, Plainsboro, both of N.J.

[73] Assignee: General Electric Company, Schenectady, N.Y.

[21] Appl. No.: 08/773,548

[22] Filed: Dec. 23, 1996

[51] Int. Cl.$^7$ ............................................... H04N 7/18
[52] U.S. Cl. ........................................... 348/77; 128/903
[58] Field of Search ....................... 348/61, 77; 128/903; H04N 7/18

[56] References Cited

U.S. PATENT DOCUMENTS

| | | | |
|---|---|---|---|
| 4,802,008 | 1/1989 | Walling | 358/141 |
| 4,945,410 | 7/1990 | Walling | 358/141 |
| 5,168,531 | 12/1992 | Sigel | 382/48 |
| 5,216,596 | 6/1993 | Weinstein | 364/413 |
| 5,297,034 | 3/1994 | Weinstein | 364/413 |
| 5,432,871 | 7/1995 | Novik | 382/232 |
| 5,642,513 | 6/1997 | Schnellinger et al. | 395/705 |
| 5,655,084 | 8/1997 | Pinsky | 395/203 |
| 5,835,735 | 11/1998 | Mason et al. | 395/287 |

OTHER PUBLICATIONS

A. Abdel–Malek et al., Article in Telemedicine Today entitled "Telemammography Feasibility," Nov.–Dec. 1996.
Kathryn E. Dudding et al., "Data Transmission Integrity Using Satellite Teleradiology Testbed for Digital Mammography," paper submitted at Third International Workshop on Digital Mammography in Chicago, IL, Jun. 10–14, 1996.
Bruce G. Barnett et al., "Satellite Teleradiology Testbed for Digital Mammography," paper presented at the SPIE Medical Imaging IX: PACS Design & Evaluation Conference, Newport Beach, CA, Feb. 10–15, 1996.
E. T. Saulnier et al., "Experience With a Proposed Teleradiology System for Digital Mammography," published in Proceedings of SPIE Medical Imaging IX: PACS Design & Evaluation, Feb. 1995.
G.T. Kuduvalli et al., "High–Resolution Digital Teleradiology: A Perspective," Journal of Digital Imaging, vol. 4, No. 4, Nov. 1991, pp. 251–261.

*Primary Examiner*—Howard Britton
*Attorney, Agent, or Firm*—John F. Thompson; Jill M. Breedlove

[57] ABSTRACT

A satellite communication system for sending high resolution medically related images from a remote location to a central location for diagnostics, consisting of at least one remote transmitting and receiving station and a central diagnostic station adapted to provide an image based on a standard digital format such as Digital Imaging and Communications in Medicine (DICOM), and the Extended Transmission Control Protocol to transmit medically related images with a transmission efficiency of at least 90 percent to facilitate feed back while the patient remains at the remote transmitting and receiving station.

24 Claims, 3 Drawing Sheets

SYSTEM AND METHOD FOR PROMPT-RADIOLOGY IMAGE SCREENING SERVICE VIA SATELLITE

RELATED APPLICATIONS AND PATENTS

This invention was made with Government support under Government Contract No. R01CA60246-02 awarded by the National Institute of Health. The government has certain rights in this invention.

BACKGROUND OF THE INVENTION

The present invention relates to a satellite based communications system for transmitting medically related images from one or more remote locations to a central station and more particularly, to a system and method for converting radiological digital images into a radio signal for transmission to a central station, then at the central station converting the signals back into video or printed images for analysis, all within a limited time.

The current clinical practice for mammography depends on a batch-mode diagnostic procedure. This batch-mode operation consists of end-of-the-day collection of data representing each patient's examination at the screening site and then transferring them via surface transportation to the radiologist's location to be loaded on the mammography viewer for the start of the detection and diagnosis process. Typically, it takes less than five minutes for the radiologist to view all images from a single patient exam before deciding whether to view past year examinations and request a magnification view of suspicious areas. The batch approach inherently does not take advantage of the five minute turnaround in which a radiologist can interpret an examination and provide a diagnosis or request that more images be taken. If the images could be evaluated as they are produced, the reader could respond with the examination results while the patient is still at the examination site. As a result, the current problem, in that about 40 percent of patients do not return for follow-up exams, would be solved because the reduced delay between image collection and interpretation so that the need for further imaging is identified before the patient departs the facility. There exists a need to conduct remote radiological exams and to provide results of the exam while the patient is still available for additional exams.

Digital radiological images typically contain a high volume of data bits. To accomplish remote imaging the high volume of digitized radiological image data must be accurately transmitted via satellite within a short period of time. Systems for transmitting, via satellite, medically related images from remote stations to a central station are not adapted to handle the high volume of data needed for applications such as remote mammography examination. For example, mammography requires high resolution imagery, usually to within a 50 micron diameter. When converted to digital images, such high resolution mammography films require digitization of about 256 million bits per image. Consequently, the ability to transmit these high volume digitized images is limited because most present day communication protocols are designed for low volume data transmissions.

The data transmission limitations of the present system also impede the possibility of interactive communications between the remote station and the central diagnostic site. By way of illustration, high resolution mammography films require digitization of about 256 million bits per image and breast mammography typically requires four images per patient; correspondingly, one giga-bit of image data is transmitted per patient. Present systems for transmission of medical data cannot transmit this volume of information within, for example, a 10.5 minute window deemed necessary for interactive communications between the remote site and the professional located at the central diagnostic site.

The American College of Radiology and National Electrical Manufacturers Association developed a communications protocol for digital radiological images called Digital Imaging and Communications in Medicine (DICOM). DICOM is a specification of vendor-independent data formats and data transfer services for digital medical images. It was designed to ensure compatibility at the data level between the various manufactures of equipment for handling digitized images. This standard is used extensively in the industry.

The Extended Transmission Control Protocol/Internet Protocol, Extended (TCP/IP), was developed by the Network Working Group, of the Internet Engineering Task Force, and published in May 1992 by V. Jacobson, R. Braden, and D. Borman. It is an Internet based communications protocol designed to tolerate unreliable sub networks. This standard is used in the industry.

It is thus desirable to provide a satellite communication system utilizing a standard digital format such as DICOM and the Extended TCP/IP protocol so as to enable a remote station to provide high resolution medical images to a central diagnostic station within a time-frame to provide an effective interactive medical exam.

SUMMARY OF THE INVENTION

The invention described herein is a satellite communication system and method for sending high resolution medically related images from a remote location to a central location for diagnostics. This invention comprises: a central diagnostic station which has transmit and receive capability, and a remote station which has transmit and receive capability. The remote station comprises a film digitizer, processor, satellite transceiver, and satellite antenna. The central diagnostic station comprises a processor, satellite transceiver, satellite antenna, and film viewer.

The processor in each station is adapted to format digitized representations of the medically related image into a standard format such as DICOM utilizing the extended TCP/IP protocol so as to transmit digital representations of the medically related image to the central diagnostic station over a satellite link wherein the transmission has at least a 90 percent efficiency rate so as to enable feedback to be provided to the remote station on an interactive basis.

The method of sending high resolution medically related images via satellite from a remote station to a central diagnostic station within a predetermined time, comprises the following steps: obtaining a digital representation of a radiology image, packing a digital representation of the image into blocks of data having a transmission efficiency of at least 90 percent for a predetermined bandwidth; transmitting the blocks of data from the remote transmitting and receiving station utilizing the extended TCP/IP protocol; receiving the blocks of data via satellite by the central diagnostic station utilizing the extended TCP/IP protocol; and converting the blocks of data into a replica of the image in a readable format.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description in conjunction with the accompanying drawings in which like characters represent like parts throughout the drawings, and in which:

DETAILED DESCRIPTION OF THE INVENTION

The Applicants' invention is comprised of two major elements: a remote transmitting and receiving station and a centralized diagnostic station. Each station communicates to the other via satellite.

Figure 1:
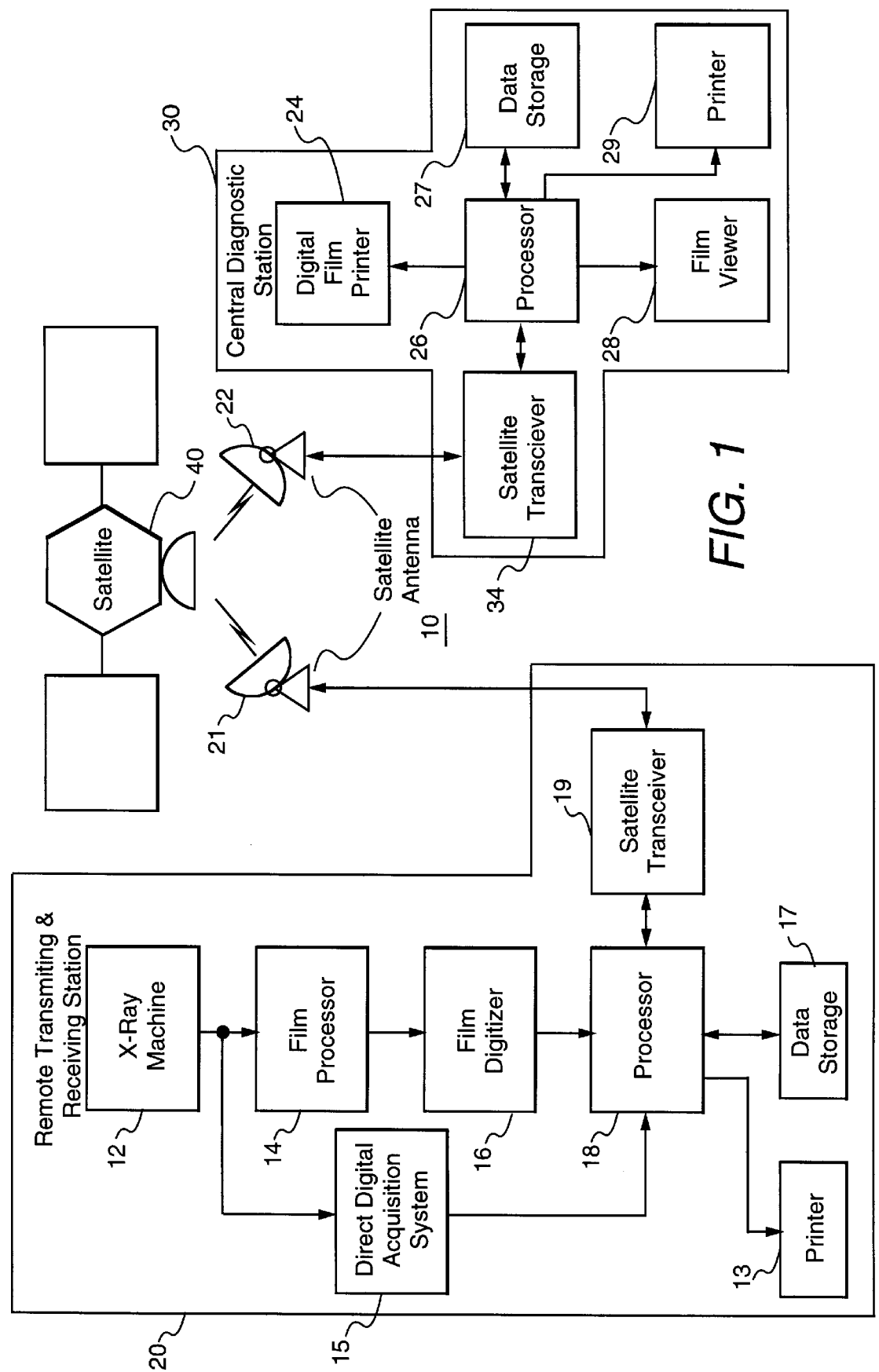
FIG. 1 is a diagram of the system architecture for prompt-radiology image screening service via satellite.

FIG. 1 shows a diagram of the system architecture 10 of the present invention. The remote transmitting and receiving station 20 can be either fixed or mobile. The remote station 20 includes either a film processor 14 and a film digitizer 16 or direct digital acquisition system 15, a processor 18, and a fixed or deployable multi-band satellite antenna 21 or combination of the above elements appropriate for preserving and transmitting the image.

Remote mobile transmitting and receiving station 20 (FIG. 1) may comprise, for example, a trailer that can be attached to a fixed transmitting and receiving station 20 as above or be towed behind a remote radiological image acquisition van housing an x-ray 12 machine and film processor 14, such as is commonly used to provide healthcare in under-served communities. Remote mobile transmitting and receiving station 20 typically comprises radiological film digitizer 16, processor 18, satellite transceiver 19, and satellite antenna 21, or any combination of these elements.

The image acquisition apparatus 15 (FIG. 1) is capable of producing images of medically related objects. Commonly the radiological images are captured on a film. When the image is on film, a film digitizer 16 is necessary to produce a digital representation of the film to facilitate processing by processor 18 and communication by satellite transceiver 19 to satellite 40.

In cases in which the radiological image is directly acquired in digital form, film digitzers are not needed for the conversion. Processor 18 (FIG. 1) converts the digital image into a standard format such as DICOM which is compatible with an extended version of TCP/IP as discussed in greater detail below. This extension of TCP/IP is utilized because it allows flexibility in choosing the size of each block of data 52 (FIG. 2) transmitted via satellite. Consequently, block of data 52 can be chosen to fill a transmission pipeline 50 as will be discussed later. As such, data can be efficiently transmitted over any compatible satellite network bandwidth.

Satellite transceiver 19 (FIG. 1) processes the digital image data such that it can be transmitted via multi-band satellite antenna 21 to satellite 40, for example, a Ka, Ku, or C band, T-1 rate satellite. Although T-1 rate satellite 40, which communicates at a rate of 1.544 mega-bits per second, is chosen for illustrative purposes, any satellite communications rate can be utilized with the present invention with a minor modification of the size of the transmitted block of data to maximize the transmission efficiency.

As shown in FIG. 1, central diagnostic station 30 comprises a multi-band satellite antenna 22, processor 26, radiological film printer 24 and film viewer 28. Multi-band antenna 22 is adapted to transmit and receive satellite based signals, particularly the Ka, Ku, or C band high bandwidth signals at the T-1 rate or higher. Processor 26 is adapted to receive the transmitted image data utilizing a standard communications format, such as DICOM. Data storage systems 17 and 27 can be employed to store digital image representations for future reference. Printer 24 prints human readable radiological films, and film viewer 28 is adapted to present the digital image files in a human readable format, such as on a computer monitor.

This invention uses processors 18 and 26 (FIG. 1) in each respective station 20 and 30 to provide control and data transfer capability. For example, a Sun® workstation is typically utilized as processor 18 in remote station 20 and processor 26 in the central diagnostic station 30. Processors 18 and 26 provide control for film digitizer 16 and satellite transceivers 19 and 34. Additionally, processors 18 and 26 may be utilized to provide control and data formatting capability for storage units 17 and 27 and printers 13 and 29 in each of the stations 20 and 30.

Remote transmitting and receiving station 20 (FIG. 1) communicates via satellite 40 with central diagnostic station 30. This network performance depends on the product of the bandwidth (i.e. the satellite communications rate) multiplied by the round-trip-time (RTT). The RTT is the time it takes an electromagnetic wave moving at the speed of light to travel from an earth based unit, to travel to and from a satellite, back to another earth based unit. The satellite is typically about 22,000 miles above the earth in geo-synchronous orbit. The T-1 satellite link has a round trip time of 513 milli-seconds, making the bandwidth delay a significant problem. For example, once remote transmitting and receiving station 20 begins to transmit a data-bit-stream it must wait 513 milliseconds for central processing station 30 to provide acknowledgment of completed transmission of block of data 52. This delay occurs because the speed of light limits the speed at which radio signal data can travel, and because satellite 40 adds delay when it receives and re-transmits the received signal. To avoid gaps in transmission remote transmitting and receiving station 20 must transmit a continuous data bit-stream for the entire 513 millisecond time.

Figure 2:
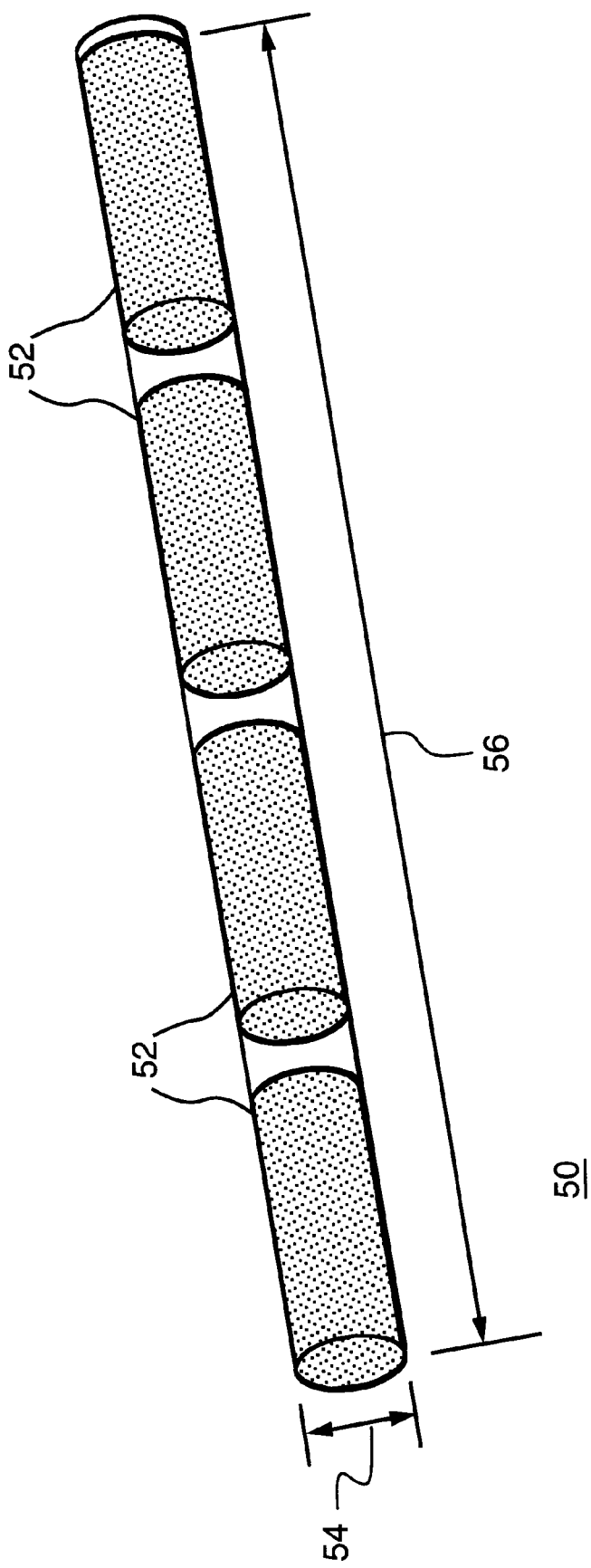
FIG. 2 is a graphic representation of the bandwidth product of the transmission bandwidth as a function of the transmission time.

This type of high bandwidth, high delay network is called a Long Fat Network (LFN). TCP extensions for LFNs were necessary to optimize use of the link, such as the Window Scaling Option described in TCP extensions for high performance, RFC1323, Network Working Group, Internet Engineering Task Force, May 1992, by V. Jacobson, R. Braden, and D. Borman. Enhanced Transmission Control Protocol/Internet Protocol (TCP/IP) is an Internet based communications protocol designed to tolerate unreliable sub networks. TCP was designed to operate reliably over most transmission mediums without regard to transmission rate, delay, corruption, duplication, or reordering of data segments. TCP performance depends not upon the transfer rate itself, but rather upon the product of the transfer rate and the round-trip-time. As depicted in FIG. 2, the Bandwidth Product is the bandwidth 54 multiplied by the RTT 56 (also depicted as pipeline 50). The bandwidth product determines the amount of data that is required to fill pipeline 50. It is the buffer space required at remote transmitting and receiving station 20 and central diagnostic station 30 to obtain maximum throughput on the TCP connection over the path. The size of each block of data 52 is chosen to fill pipeline 50 and yet not cause inefficiency when block of data 52 is requested to be re-transmitted because of receiving errors. Put another way, it is the amount of unacknowledged data that TCP must handle in order to keep pipeline 50 full. The extended TCP/IP protocol is capable of processing a long fat network. The extended TCP option changes a sixteen bit header field to thirty-two bits which increase the size of the window from about 65,000 bytes to about one giga-byte. Utilizing this window scale option the window size block of data 52 was determined to be about 98,000 bytes for high resolution medically related image data. The TCP/IP protocol utilized in this invention operates on data formatted using the DICOM standard.

The DICOM standard was selected because it allows the medical imaging program to communicate in a reliable and consistent manner between various medical equipment vendors who adhere to the DICOM standard. Although the DICOM standard defines a seven layer communications profile, the primary interest is the application layer interface. At this level the standard defines two key ingredients that enable conforming programs to operate together. First, it defines the syntax and the semantics of information elements that are to be exchanged between communications programs. Second, it defines the behavior associated with individual services that communicating entities provide or invoke as well as the syntax and semantics associated with the messages that need to be exchanged. In the case of mammography digital images, the Secondary Capture Information Object definition was used, because it provides a method for capturing the raw pixel data associated with image attributes.

The present invention incorporates a transmission rate with an efficiency over 90%. The scale factor in the long fat network has been set to allow a transmission of one block of data 52 (FIG. 2) or about 98,000 bytes per RTT. This scale factor was chosen because the RTT and Bandwidth product defines the maximum transmission possible. As shown in FIG. 2, the T-1 based satellite has a RTT of 513 milliseconds and the Transmission rate is 1.544 mega-bits per second. Together these numbers define the bandwidth-product of 792,072 bits or 98,496 bytes. (1.544 mega-bits/sec*513 milliseconds). After accounting for overhead the TCP/IP protocol can transmit about 96,000 digital image data bytes per RTT. Consequently, the transmission rate efficiency is 96,000 bytes of data divided by the 98,000 byte window available for transmission per RTT, or about 98 percent.

In the case of high resolution digital mammographic images, each image is about 4000×4000×16 bits (256 mega-bits or 32 mega-bytes), which is sufficient to detect a spot in an image with a fifty micron diameter. Resolution of this level allows micro calcification structures in a digital mammogram to be detected because every two bytes of digital image data represents a diameter of about fifty microns on the medically related film. Using the T-1 rate of transmission the present invention transmits a single digital mammogram in about three minutes under the above described conditions. While a T-1 rate calculation has been illustrated by way of example, any satellite data transmission rate could have been employed.

Again by way of example, a typical x-ray mammography machine operating for seven hours can accommodate forty patient exams per day, in which each exam takes four mammogram images. The typical duration of an exam is ten and one-half minutes. A bandwidth of 1.63 mega bits per second would be required without using compression to transmit the full set of four images to central diagnostic station 30 (FIG. 1) in about ten and one-half minutes. This bandwidth cannot be supported with T-1 rate satellite 40. Accordingly, data can be compressed using a compression technique, such as Lempel-Ziv lossless compression. Lempel-Ziv lossless compression compresses the object data such that each bit can be decompressed without the loss of any single bit of data. Once the data is compressed the volume of data bits generated from an radiology image is reduced. This reduced volume results in a decreased need for transmission time and storage space. A lossy technique could also be employed to compress digital data. The lossy compression technique further reduces the volume of data form an image than a lossless technique. Because the image data volume is further reduced less storage space is required and transmission time is further reduced. However, with lossy compression all data bits cannot be regenerated when the image data is decompressed. As such, the lossy technique is less preferred than the lossless technique, however, the lossy technique can be used when data images are transmitted to central diagnostic station 30 for diagnoses and don't need resolution to the fifty micron level. Minimum data compression to meet the ten and one-half minute window is 1.06 to 1. Lossless compression is usually preferred because of the fifty micron detection requirement making each bit critical to mammogram diagnosis. A hardware data compression solution is used to minimize the delay imposed by the compression and decompression algorithms. However, a software data compression technique could be used. For example, using a data compression factor of 1.75 to 1 with the present invention, and assuming a typical exam duration of 10.5 minutes, the transmission time of data representing a single mammogram image is 2.26 minutes. Thus, if four images are transmitted the total time of transmission time is about nine minutes. As such, the system is able to transmit four exam images before the typical exam is complete. This allows the radiologist to communicate the results of the exam back to the remote station while the patient remains in the exam room. This communication would involve providing a favorable result or requesting that more images be taken. Therefore using the present invention there is no queuing delay (i.e. the delay caused when images have to wait for the previous batch to finish transmission).

This invention is also effective without the use of data compression. Since each image can be transmitted within about three minutes, it would take about twelve minutes to transmit a full set of patient images at the T-1 rate. Although this transmission is not completed in the average exam time, it would add only about one and one-half minutes of delay in the typical exam. As such, the transmission of image data without utilizing data compression is near real time. Also, if a transmission rate greater than 1.63 Mega-bits per second is used, a full set of images could be transmitted the central diagnostic station within the typical exam time of ten and one-half minutes.

Figure 3:
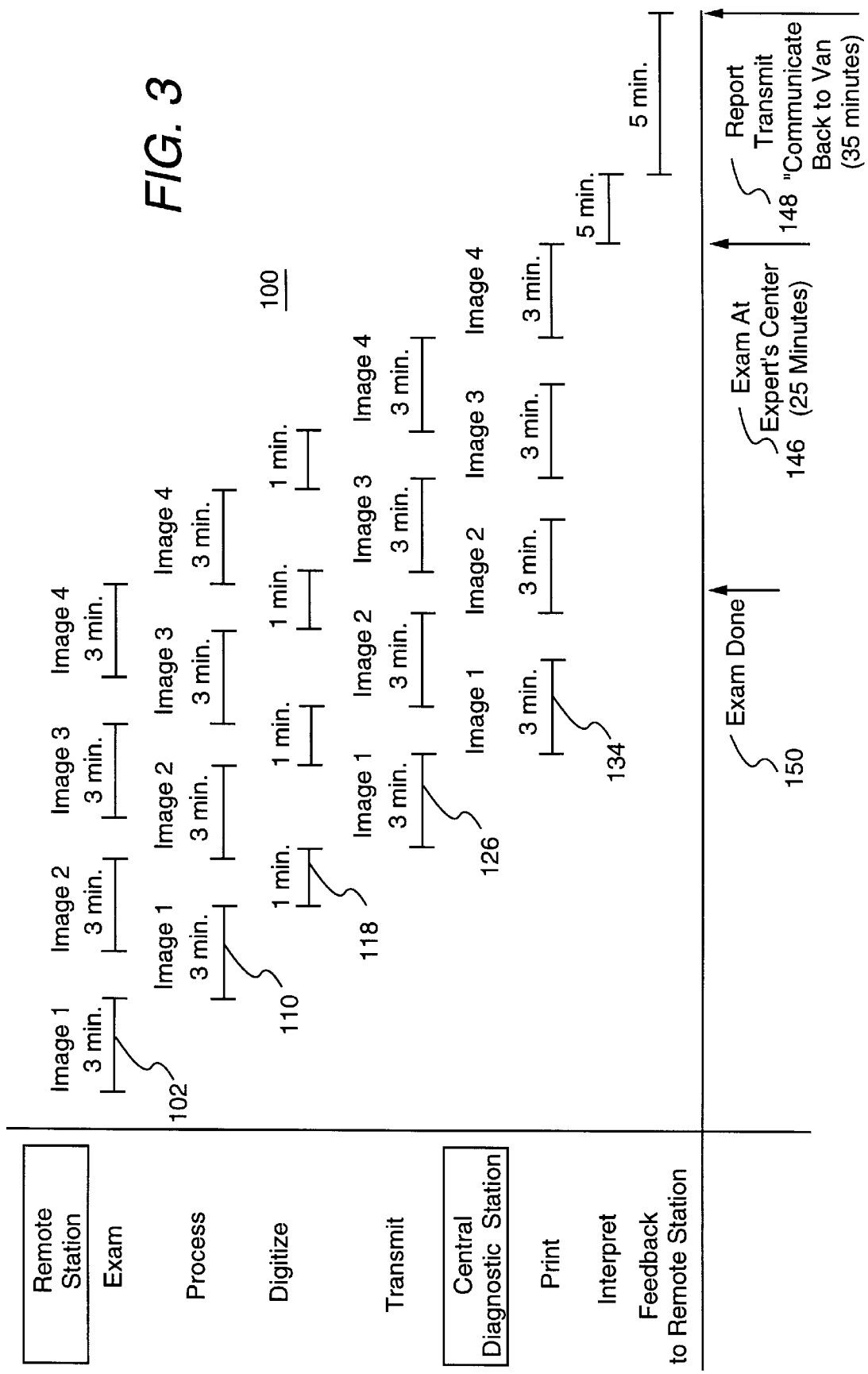
FIG. 3 is a graphic illustration of time sequence of events of the typical breast mammography exam utilizing the present invention.

The process of the present invention is represented in FIG. 3. A patient enters an x-ray exam room where a first image is taken using x-ray equipment 12 (FIG. 1), this evaluation takes approximately three minutes 102 (FIG. 3). Next, the first image is processed and a film of the image is made using film equipment 14 (FIG. 1). This step takes an additional three minutes 110 (FIG. 3). Next, the first image is digitized by film digitizer 16 which takes about one minute 118 (FIG. 3). Next the first image is processed and transmitted to central diagnostic station 30 (FIG. 1) via T-1 rate satellite 40, a process that takes about three minutes 126 (FIG. 3) utilizing the DICOM standard with the extended TCP/IP protocol. Although remote transmitting and receiving station 20 (FIG. 1) may not house x-ray machine 12, or film processor 14, the films could be provided from some other source.

As is shown in FIG. 3, just after the first image is taken using mammography equipment 12 (FIG. 1), a second image is taken. This image then follows the same steps as the first image. Subsequently, a third and a forth image is taken and transmitted to central diagnostic station 30 using the same procedure as the first image. The entire process, from acquisition of first image at remote transmitting and receiving station 20 (FIG. 1) to the receipt of the fourth image at the central diagnostic station 30, takes approximately twenty-seven minutes nominally 146 (FIG. 3).

Central diagnostic station 30 (FIG. 1) receives the first image. This image is then sent to film viewing apparatus 28 which converts the image to a human readable format. This apparatus can either be a film viewer 28 which displays the digital image or radiological film printer 24 which prints the image in a human readable format. Film viewer 28 could also be a film maker which makes a x-ray type film based on the digital image. The second, third, and forth image are similarly received and converted to human readable formats. A radiologist or similarly qualified person interprets the images and sends the results back to remote transmitting and receiving station 20 via satellite 40. The feedback communications from central diagnostic station 30 may be provided in a standard medical reporting format. The entire process, from acquisition of the first image to receipt and report at remote transmitting and receiving station 20, takes about twenty-seven minutes 148 (FIG. 3).

A significant reduction in the twenty-seven minute process time described above will result when the radiological images are directly acquired utilizing the direct digital acquisition system 15 (FIG. 1) rather that x-ray films being created and digitized by the film processor 14 and film digitizer 16. When the images are acquired from direct digital acquisition system 15 there is no need for film development and subsequent film digitization. This short-cut results in a savings of four minutes per image—a significant reduction in process time.

The method of sending high resolution, medically related images, via satellite, from remote transmitting and receiving station 20 (FIG. 1) to central diagnostic station 30 within thirty-two minutes, comprises the following steps: obtaining a digital representation of a radiology image, packing digitized representations of an image into a block of data having a transmission efficiency of at least 90 percent for a T-1 bandwidth or higher; transmitting the digitized block of data from remote transmitting and receiving station 20 utilizing the extended TCP/IP protocol; receiving the block of data via satellite 40 by central diagnostic station 30 utilizing the extended TCP/IP protocol; and converting the block of data into a readable format.

It will be apparent to those skilled in the art that, while the invention has been illustrated and described herein in accordance with the patent statutes, modifications and changes may be made in the disclosed embodiments without departing from the true spirit and scope of the invention. It is, therefore, to be understood that the appended claims are intended to cover all such modifications and changes as fall within the true spirit of the invention.

What is claimed is:

1. A satellite communication system for sending high resolution medically related images from a remote location to a central location via satellite, said satellite communication system comprising:
   at least one remote transmitting and receiving station, said at least one remote transmitting and receiving station transmitting via satellite digital image data comprising a digital representation of said high resolution medically related images;
   at least one central transmitting and receiving diagnostic station linked via said satellite to said at least one remote transmitting and receiving station, said at least one central transmitting and receiving diagnostic station receiving said digital image data;
   each of said stations comprising:
      a processor wherein said processor provides an extended TCP/IP protocol for transmitting and receiving said digital image data via satellite with an efficiency of at least 90 percent.

2. A satellite communications system as recited in claim 1, wherein said TCP/IP protocol is further based on a Digital Imaging and Communications in Medicine (DICOM) standard.

3. A satellite communications system as recited in claim 1, wherein said remote transmitting and receiving station further comprises at least one digitizing apparatus coupled to said processor, a remote station satellite transceiver coupled to said processor, and a satellite antenna coupled to said remote station satellite transceiver.

4. A satellite communications system as recited in claim 3, wherein said digitizing apparatus further comprises a digital data acquisition system.

5. A satellite communications system as recited in claim 3, wherein said digitizing apparatus further comprises a film digitizer.

6. A satellite communications system as recited in claim 1, wherein said central diagnostic station further comprises at least a central station satellite transceiver coupled to said central station processor, a satellite antenna coupled to said satellite transceiver, and a film viewing apparatus coupled to said processor.

7. A satellite communications system as recited in claim 6, wherein said film viewing apparatus further comprises a film maker.

8. A satellite communications system as recited in claim 7, wherein said film viewing apparatus further comprises a radiological film printer.

9. A satellite communication system as recited in claim 1, wherein said central station transceiver transmits diagnostic results to said remote transmitting and receiving station via said satellite.

10. A satellite communication system as recited in claim 1, wherein said remote transmitting and receiving station transceiver receives diagnostic results from said central diagnostic station via said satellite.

11. A satellite communication system as recited in claim 1, wherein each of said processors compress and process digital data for each image into said extended TCP/IP protocol.

12. A satellite communication system as recited in claim 11, wherein each of said processors is compress said digital images without introducing error.

13. A satellite communication system as recited in claim 12, wherein each of said processors unpack digital images utilizing a decompressor.

14. A satellite communication system as recited in claim 13, wherein each of said processors decompress said digital images without introducing error.

15. A satellite communication system as recited in claim 1, wherein each of said processors provide said TCP/IP protocol for transmitting and receiving digital image data with an efficiency of about 98 percent.

16. A method of sending high resolution, medically related images from a remote transmitting and receiving station to a central transmitting and receiving diagnostic station within a predetermined time via satellite, the method comprising the following steps:

packing digitized representations of an image into at least one block of digital data;

transmitting the packed at least one block of digital data from said remote transmitting and receiving station utilizing an extended TCP/IP protocol via satellite;

receiving the transmitted at least one block of digital data via satellite by said central transmitting and receiving diagnostic station utilizing said extended TCP/IP format; and converting the received at least one block of digital data into a readable format.

17. A method of sending high resolution, medically related images as recited in claim 16, wherein said extended TCP/IP protocol is further based on a DICOM standard.

18. A method of sending high resolution, medically related images as recited in claim 16, wherein said at least one block of digital data is further selected to have a transmission utilization efficiency of at least 90 percent for a predetermined bandwidth and a predetermined round trip transmission delay.

19. A method of sending high resolution, medically related images as recited in claim 18, wherein said at least one block of digital data is further selected to have a transmission utilization efficiency of at about 98 percent for a predetermined bandwidth and a predetermined round trip transmission delay.

20. A method of sending high resolution, medically related images as recited in claim 18, wherein said digitized representation of said image is further compressed before being transmitted and decompressed after being transmitted.

21. A method of sending high resolution, medically related images as recited in claim 20, wherein said digitized representation of said image is further compressed without introducing compression errors.

22. A method of sending high resolution, medically related images as recited in claim 20, wherein said digitized representation of said image is further decompressed without introducing decompression errors.

23. A satellite communication system for transmitting high resolution medically related images via satellite, said satellite communication system comprising:

a remote transmitting and receiving station comprising:
    a remote station processor providing an extended TCP/IP protocol;
    a digitizing apparatus coupled to said remote station processor, said digitizing apparatus creating digital image data from said high resolution medically related images;
    a remote station satellite transceiver coupled to said remote station processor; and
    a remote station satellite antenna coupled to said remote station transceiver, said remote station satellite transceiver and said remote station satellite antenna transmitting said digital image data using said extended TCP/IP protocol;

a central diagnostic station connected via said satellite to said remote transmitting and receiving station, said central diagnostic station comprising:
    a central station processor;
    a central station satellite transceiver coupled to said central station processor;
    a central station antenna coupled to said central station satellite transceiver, said central station satellite transceiver and said central station satellite antenna receiving said digital image data;
    an image viewing apparatus coupled to said central station processor, said image viewing apparatus displaying said high resolution medically related image processed from said digital image data by said central station processor.

24. A method for transmitting via satellite high resolution, medically related images from a remote transmitting and receiving station to a central transmitting and receiving station, said method comprising the steps of:

packing digitized representations of said images into at least one block of digital data;

compressing said digital data without introducing compression errors;

transmitting said compressed digital data from said remote transmitting and receiving station via satellite using an extended TCP/IP protocol;

receiving said transmitted digital data via said satellite at said central transmitting and receiving station;

decompressing said received digital data without introducing decompression errors; and converting said decompressed digital data into a readable format.

* * * * *